(12) United States Patent
Ozawa et al.

(10) Patent No.: US 8,761,471 B2
(45) Date of Patent: Jun. 24, 2014

(54) MEDICAL IMAGE DIAGNOSIS DEVICE THAT GENERATES A REFERENCE IMAGE FROM A FLUOROSCOPIC MASK IMAGE

(75) Inventors: Masahiro Ozawa, Sakura (JP); Toshiya Waku, Yaita (JP); Masanori Matsumoto, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 158 days.

(21) Appl. No.: 13/390,699

(22) PCT Filed: Oct. 13, 2011

(86) PCT No.: PCT/JP2011/005732
§ 371 (c)(1),
(2), (4) Date: Feb. 16, 2012

(87) PCT Pub. No.: WO2012/049850
PCT Pub. Date: Apr. 19, 2012

(65) Prior Publication Data
US 2012/0148139 A1 Jun. 14, 2012

(30) Foreign Application Priority Data
Oct. 14, 2010 (JP) .................................. 2010-231534

(51) Int. Cl.
*G06K 9/00* (2006.01)
(52) U.S. Cl.
USPC .......................................................... 382/128
(58) Field of Classification Search
None
See application file for complete search history.

(56) References Cited

U.S. PATENT DOCUMENTS

| 7,412,023 B2 * | 8/2008 | Ohishi et al. ...................... 378/4 |
| 2002/0045817 A1 * | 4/2002 | Ichihashi ....................... 600/425 |
| 2006/0241369 A1 | 10/2006 | Lienard et al. |
| 2008/0232548 A1 * | 9/2008 | Tanaka .......................... 378/98.2 |

(Continued)

FOREIGN PATENT DOCUMENTS

| CN | 101422370 A | 5/2009 |
| JP | 2003-143479 A | 5/2003 |

(Continued)

OTHER PUBLICATIONS

International Preliminary Report on Patentability and Written Opinion issued May 16, 2013 in PCT/JP2011/005732 filed on Oct. 13, 2011.

(Continued)

*Primary Examiner* — Tahmina Ansari
(74) *Attorney, Agent, or Firm* — Oblon, Spivak, McClelland, Maier & Neustadt, L.L.P.

(57) ABSTRACT

A medical image diagnosis device according to an embodiment includes: a mask image generation unit that generates a plurality of mask images that are different in terms of time; a first image generation unit that calculates differences between a plurality of the mask images, and extracts an image of a preceding device that is placed and kept in a blood vessel; a second image generation unit that generates a real-time fluoroscopic image depicting a situation where an insertion device is being inserted into a blood vessel, calculates a difference between the real-time fluoroscopic image and the mask image, and generates an image of the insertion device; an image synthesis unit that synthesizes images generated by the first image generation unit and the second image generation unit; and a display unit that displays an image generated by the image synthesis unit.

10 Claims, 5 Drawing Sheets

(56) References Cited

U.S. PATENT DOCUMENTS

| | | |
|---|---|---|
| 2009/0022262 A1 | 1/2009 | Ohishi |
| 2009/0180591 A1* | 7/2009 | Baumgart ................ 378/98.12 |
| 2009/0192385 A1* | 7/2009 | Meissner et al. ............. 600/426 |
| 2010/0172474 A1* | 7/2010 | Vogt et al. ................ 378/98.12 |
| 2010/0208973 A1* | 8/2010 | Lienard et al. ................ 382/132 |
| 2010/0329526 A1* | 12/2010 | Pfister et al. ................ 382/130 |
| 2011/0033102 A1* | 2/2011 | Zhu et al. ...................... 382/134 |
| 2011/0311113 A1* | 12/2011 | Baumgart ...................... 382/128 |
| 2012/0148139 A1* | 6/2012 | Ozawa et al. ................ 382/132 |
| 2013/0034283 A1* | 2/2013 | Ohishi ......................... 382/128 |

FOREIGN PATENT DOCUMENTS

| | | |
|---|---|---|
| JP | 2004-208306 A | 7/2004 |
| JP | 2007-125240 A | 5/2007 |
| JP | 2007 229473 | 9/2007 |
| JP | 2009-39521 A | 2/2009 |

OTHER PUBLICATIONS

Office Action (with partial English translation) issued on Dec. 17, 2013, in counterpart Chinese Appln No. 201180003347.6 (8 pages).

\* cited by examiner

| Insertion order | Coil | Shape | Size |
|---|---|---|---|
| 1 | DCS | Complex Fill | 8×24 |
| 2 | DCS | Complex Fill | 8×15 |
| 3 | DCS | Complex Fill | 7×21 |
| 4 | DCS | Complex Fill | 7×13 |
| 5 | DCS | Complex Fill | 6×15 |
| 6 | DCS | Complex Fill | 6×9 |
| 7 | DCS | Complex Fill | 5×15 |
| 8 | GDC | 10-ultrasoft SR | 4×6 |
| 9 | GDC | 10-ultrasoft SR | 4×6 |
| 10 | GDC | 10-ultrasoft SR | 2×3 |

MEDICAL IMAGE DIAGNOSIS DEVICE THAT GENERATES A REFERENCE IMAGE FROM A FLUOROSCOPIC MASK IMAGE

TECHNICAL FIELD

Embodiments of the present invention relate to a medical image diagnosis device and medical diagnosis support method that process a fluoroscopic mask image and a fluoroscopic image, which is captured in real time, to provide a reference image to a practitioner who operates a catheter or any other device.

BACKGROUND ART

In an interventional treatment (intravascular treatment), which is one kind of treatment for aneurysms, or in an angiographic examination, a catheter is inserted into a blood vessel for example from the groin until the catheter goes through the blood vessel to reach a target part. For a process of sending the catheter (or a guide wire for guiding the catheter) to a target location, there has been a roadmap function that superimposes an X-ray fluoroscopic image on a 3D (three-dimensional) vascular image displaying the image. A practitioner can lead the catheter or guide wire to an affected part while viewing a displayed roadmap. The roadmap function is expected to be effective in reducing the examination time and the amount of a contrast agent.

As one kind of treatment for cerebral aneurysms, there is a method of putting a coil-like obstructive material into an aneurysm from the tip of a catheter and keeping the obstructive material therein to cause blood to clot in the aneurysm and block the flow of blood, thereby preventing the rupture of the aneurysm. The treatment method is typically referred to as coiling. In a coiling operation, the displaying of a 3D roadmap, for which a previously reconstructed 3D vascular image is used as a map, is effective. By the way, in the coiling, first a coil of a large size is placed and kept. Then, a coil of a small size is placed and kept in order to gradually close a gap.

However, in the conventional way of displaying a 3D roadmap, it is difficult to distinguish between an already separated coil and a new coil that will be placed and kept. Therefore, the disadvantage is that it is difficult to figure out the state of a coil that is already placed and kept.

CITATION LIST

Patent Literature

PTL 1: Japanese Patent Application Laid-Open No. 2007-229473

SUMMARY OF THE INVENTION

Technical Problem

An object to be achieved by the present invention is to provide a medical image diagnosis device and medical diagnosis support method that improve the visibility of a device, such as a catheter, guide wire or coil.

Solution to Problem

A medical image diagnosis device of an embodiment of the present invention includes: an imaging unit that includes an X-ray generation unit and an X-ray detection unit; a mask image generation unit that generates a plurality of mask images that are different in terms of time by processing an image taken by the imaging unit; a first image generation unit that calculates differences between a plurality of the mask images, and extracts an image of a preceding device that is placed and kept in a blood vessel; a second image generation unit that generates a real-time fluoroscopic image depicting a situation where an insertion device is being inserted into a blood vessel, calculates a difference between the real-time fluoroscopic image and the mask image, and generates an image of the insertion device; an image synthesis unit that synthesizes an image generated by the first image generation unit and an image generated by the second image generation unit; and a display unit that displays an image generated by the image synthesis unit.

DESCRIPTION OF EMBODIMENTS

Figure 1:
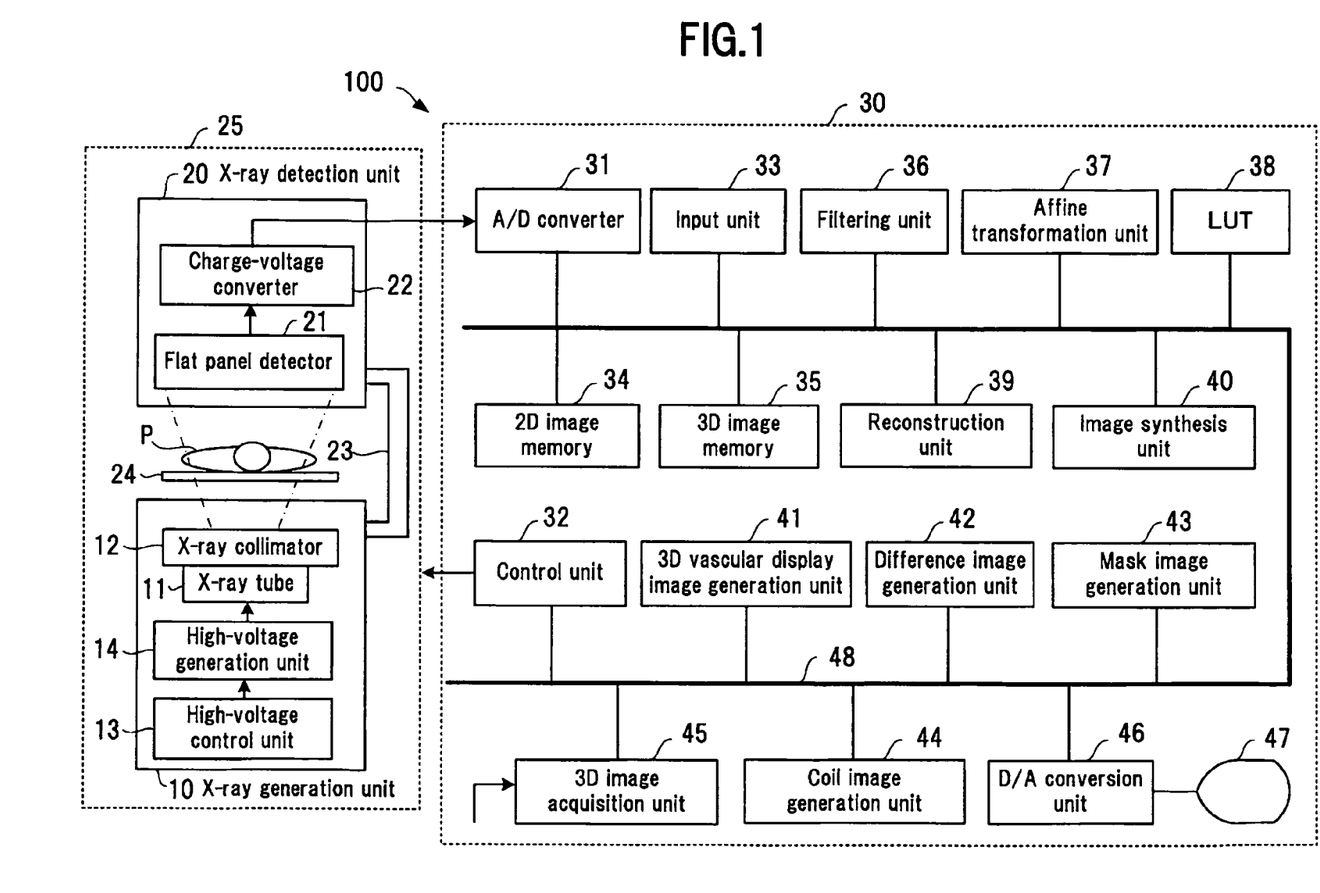
FIG. 1 is a block diagram showing the configuration of a medical image diagnosis device according to an embodiment.

Hereinafter, a medical image diagnosis device of an embodiment will be described in detail with reference to the accompanying drawings. Incidentally, in each diagram, the same parts are denoted by the same reference symbols.
(First Embodiment)
FIG. 1 is a block diagram showing the configuration of a medical image diagnosis device according to one embodiment. The medical image diagnosis device shown in FIG. 1 is, for example, an X-ray image diagnosis device 100 called an angiography device, and includes an X-ray generation unit 10, which generates X-rays for a subject P, and an X-ray detection unit 20, which detects X-rays that have passed through the subject P in a two-dimensional manner and generates X-ray projection data on the basis of the detection results.

The X-ray generation unit 10 includes an X-ray radiation unit having an X-ray tube 11 and an X-ray collimator 12, a high-voltage control unit 13, and a high-voltage generation unit 14. The X-ray tube 11 is a vacuum tube that generates X-rays, the X-ray tube 11 generates X-rays by using a high voltage to cause electrons emitted from a cathode (filament) to accelerate and strike against a tungsten anode. The high-voltage control unit 13 controls the high-voltage generation unit 14 in accordance with an instruction signal from a control unit 32 (described below), and takes control of X-ray radiation conditions, such as a tube current of the X-ray tube 11, a tube voltage, X-ray pulse width, a radiation cycle, an imaging section, and radiation time.

The X-ray detection unit 20 includes a flat panel detector (Flat Panel detector) 21, and a charge-voltage converter 22, which converts a charge read from the flat panel detector 21 into a voltage. An output of the charge-voltage converter 22 is supplied to an A/D converter 31 (described below). The X-ray generation unit 10 and the X-ray detection unit 20 are supported by an arm (C-arm) 23.

The C-arm 23 is able to move in the direction of a body axis of the subject P placed on a top panel 24 of a bed and also able to rotate around the body axis of the subject P. Incidentally, the X-ray generation unit 10 and the X-ray detection unit 20 constitute an imaging unit 25. As the C-arm 23 rotates, the imaging unit 25 circles around the subject P and is able to take pictures of the subject P in different angular directions.

Incidentally, for the X-ray detection unit 20, a combination of an image intensifier and a TV camera may be used.

The X-ray detection unit 20 is connected to an image processing device 30. The image processing device 30 includes the A/D (analog-digital) converter 31, the control unit 32, an input unit 33, a two-dimensional image memory 34, a three-dimensional image memory 35, a filtering unit 36, an affine transformation unit 37, a LUT (Look-up table) 38, a reconstruction unit 39, and an image synthesis unit 40.

The image processing device 30 further includes a three-dimensional vascular display image generation unit 41, a difference image generation unit 42, a mask image generation unit 43, a coil image generation unit 44, a three-dimensional image acquisition unit 45, a D/A (digital-analog) converter 46, and a display unit (display 47).

The A/D converter 31 converts analog outputs of the charge-voltage converter 22 to digital signals. The control unit 32 includes a CPU and a storage circuit (not shown), takes overall control of each unit of the X-ray image diagnosis device 100 via a bus line 48 on the basis of input information, setting information and selection information from the input unit 33.

The input unit 33 is designed to allow a doctor or any other user to input various commands and other kinds of information; and has an interactive interface equipped with an input device, such as a mouse, keyboard, trackball or joystick, a display panel, various switches, or the like. The input unit 33 is also used to set the traveling direction and speed of the top panel 24, to set the rotational/travelling directions and rotational/traveling speeds of the imaging unit 25, to set X-ray radiation conditions including a tube voltage and a tube current, and to perform other processes. The input unit 33 includes a roadmap switch and a fluoroscopic image collection button.

The two-dimensional image memory 34 stores two-dimensional X-ray image data and the like. The two-dimensional image memory 34 stores two-dimensional X-ray image data, which are obtained after the filtering unit 36 filters two-dimensional X-ray image data obtained by the imaging unit 25, two-dimensional X-ray image data, which have been subjected to affine transformation such as image magnification/movement in the affine transformation unit 37, and the like.

The three-dimensional image memory 35 stores a three-dimensional image, which is obtained after the reconstruction unit 39 reconstructs two-dimensional X-ray image data obtained by the imaging unit 25. The three-dimensional image memory 35 also stores a three-dimensional image obtained from external CTA (Computed Tomography Angiography), MRA (Magnetic Resonance Angiography) or the like.

The three-dimensional vascular display image generation unit 41 reads a three-dimensional image stored in the three-dimensional image memory 35, and generates, from the three-dimensional image that the three-dimensional vascular display image generation unit 41 has read, a three-dimensional vascular display image (3D volume rendering image). For example, the three-dimensional vascular display image (3D volume rendering image) is generated by performing processes, such as volume-rendering, in a way that matches a situation represented by information, such as an observation angle, observation field of view, observation magnification rate and observation location.

The difference image generation unit 42 calculates a difference between a fluoroscopic image (real-time fluoroscopic image), which is captured in real time, and a fluoroscopic mask image from the mask image generation unit 43, and generates an image of insertion devices, such as a guide wire or catheter.

The mask image generation unit 43 generates, based on image data stored in the two-dimensional image memory 34, a fluoroscopic mask image that depicts the situation where a device have not yet been inserted. Incidentally, if a coil (obstructive material) is placed and kept, then what is obtained is a fluoroscopic mask image containing the coil. The device is operated by a doctor or the like and therefore moves constantly, meaning that a difference image does not disappear when the difference is calculated by the difference image generation unit 42. Therefore, it is possible to extract a device image of a guide wire, catheter or the like. As for the output of the difference image generation unit 42, it is possible to highlight a guide wire or the like through noise suppression or higher-harmonic-wave emphasis. It is also possible to display the device image in a different color from the real-time fluoroscopic image and the three-dimensional vascular image.

The coil image generation unit 44 carries out subtraction of the previous fluoroscopic mask image generated by the mask image generation unit 43 and the latest mask image to generate an image of a preceding device such as a coil being placed and kept in a blood vessel.

The three-dimensional image acquisition unit 45 acquires a three-dimensional image (three-dimensional vascular image, for example) from outside. If the three-dimensional image acquired from outside contains any human-body information other than vascular information, a vascular information extraction unit extracts vascular information by threshold-value processing, specifying a range of pixel values, region growing or any other method (or a combination of the methods described above).

The image synthesis unit 40 synthesizes the image of the device, the three-dimensional vascular display image, the real-time image, and the coil image in a cumulative manner. The transparency rate of each image can be changed appropriately depending on doctors' and other device operator's objectives. For example, in order to figure out the motion of a guide wire or the like, it is possible to increase the visibility of the guide wire by making the layer of the guide-wire image non-transparent at the start of the fluoroscopic operation, as well as to make the layers of vascular and other images transparent.

It is also possible to change the transparency rate of each image's layer in chronological order. Moreover, it is possible to increase the visibility by making the real-time image non-transparent as a device is inserted. The look-up table 38 assigns a unique color to a roadmap portion of the composite image.

The D/A converter 46 performs D/A (Digital/Analog) conversion of the composite image (display data) to generate an image signal, which is then displayed on the display 47 such as liquid crystal.

Figure 2:
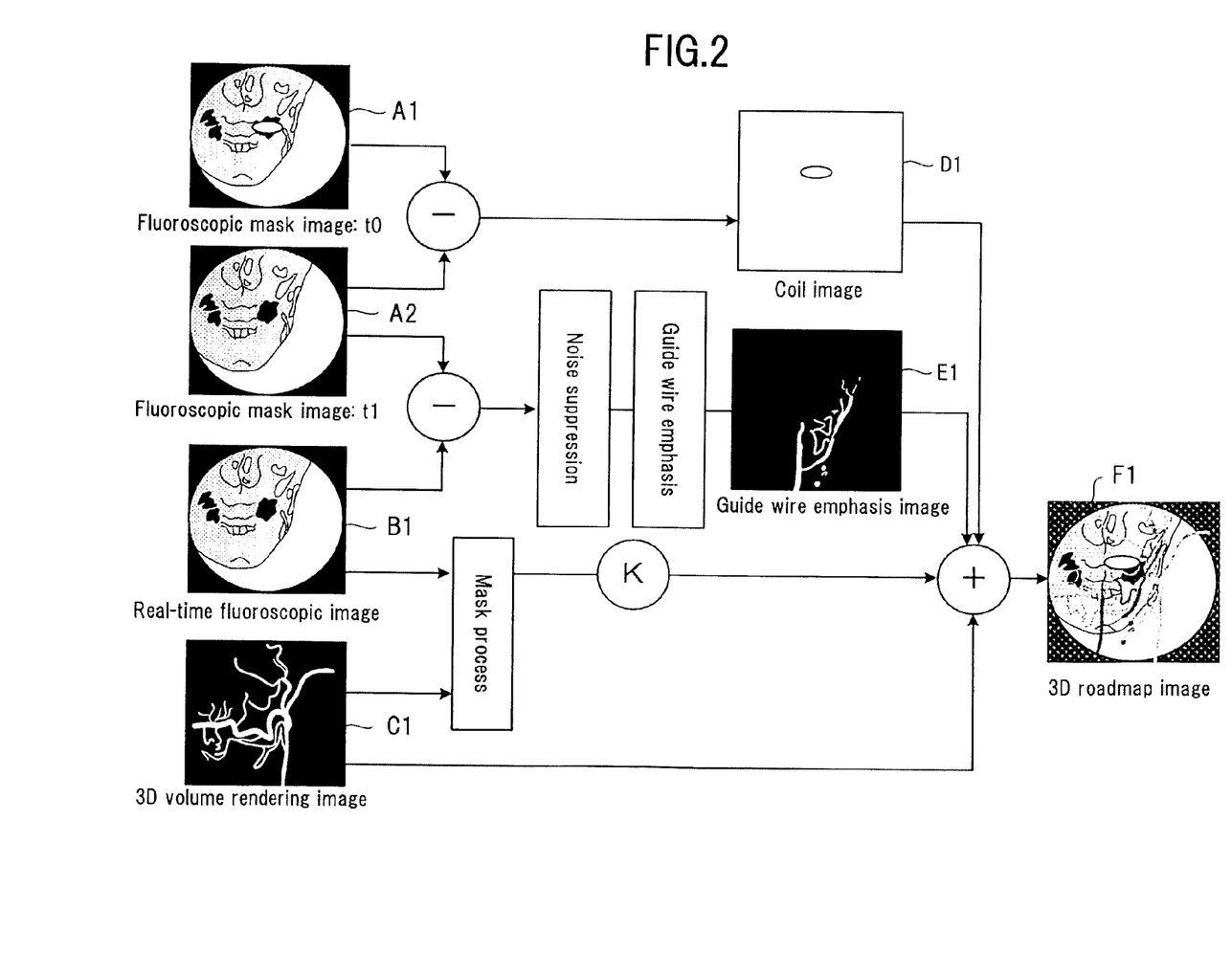
FIG. 2 is an explanatory diagram showing a process of generating a roadmap image according to the embodiment.

The following describes an operation of the medical image diagnosis device of the first embodiment. FIG. 2 is a diagram for explaining the operation, showing a process of generating a roadmap image to be displayed on the display 47. For example, in the treatment of cerebral aneurysms, coils (obstructive materials) of different sizes are placed and kept in the cerebral aneurysms. And, in the coiling operation, the displaying of a 3D roadmap is carried out with a previously reconstructed 3D vascular image as a map.

First, a coil is placed and kept. Each time a coil is placed and kept, a fluoroscopic mask image is re-created. For example, by carrying out subtraction between a previous fluoroscopic mask image A1 and the latest fluoroscopic mask image A2, it is possible to obtain for example a coil image D1, which is an image obtained by extracting a preceding device, such as a coil placed and kept within a certain period of time. That is, since a time t0 when the fluoroscopic mask image A1 is created is different from a time t1 when the latest fluoroscopic mask image A2 is created, the subtraction allows the preceding device, which is an obstructive material such as a coil placed and kept in advance within a certain period of time, to be extracted, making it possible to obtain an image of the preceding device (which is for example the coil image D1). Incidentally, what is placed and kept in a blood vessel is not limited to a coil, a stent may be placed and kept therein. In such a case, what is obtained is an image of preceding devices including a coil and a stent. In the following description, a coil image is used as an example to explain an image of a preceding device.

Moreover, by carrying out subtraction between the latest fluoroscopic mask image A2 and a real-time fluoroscopic image B1, it is possible to obtain an image of devices including a coil that will be placed and kept. That is, the real-time fluoroscopic image B1 is an image depicting the situation where devices (a catheter equipped with a coil, and a guide wire) are being inserted into a blood vessel. Therefore, the subtraction between the real-time fluoroscopic image B1 and the latest fluoroscopic mask image A2 makes it possible to obtain an image of devices including a coil that will be placed and kept (an image of insertion devices).

FIG. 2 shows a guide wire emphasis image E1 as an insertion-device image. That is, by performing noise suppression and guide wire emphasis processes on a subtraction image of the latest fluoroscopic mask image A2 and real-time fluoroscopic image B1, the image E1 with the emphasized guide wire is obtained.

Moreover, by performing a mask process on the real-time fluoroscopic image B1 and a 3D volume rendering image C1, synthesizing the images at a predetermined ratio k, and synthesizing the coil image D1 and the guide wire emphasis image E1, it is possible to obtain a 3D roadmap image F1. With the 3D roadmap image F1, it is possible to figure out the motion of the guide wire or the like, and display a coil that has already been placed and kept and a coil that is being placed and kept in such a way that the coils can be distinguished from one another, resulting in an increase in visibility. Moreover, at the time of synthetic displaying, images can be displayed in distinguishable colors or transparency rates with varying color tones, some of the images may be selected by settings so as to be displayed or not displayed. As for the 3D volume rendering image C1, a three-dimensional image acquired by an external CT device, a MRI device or any other modality may be used.

The fluoroscopic mask images A1 and A2 are generated by the mask image generation unit 43, and the 3D volume rendering image C1 by the three-dimensional vascular display image generation unit 41. The subtraction of the fluoroscopic mask images A1 and A2 is performed by the coil image generation unit 44, and the subtraction of the fluoroscopic mask image A2 and the real-time fluoroscopic image B1 by the difference image generation unit 42. The process of synthesizing each image is carried out by the image synthesis unit 40.

Incidentally, on the coil image D1, artifacts may appear due to the movement of a patient's body or the like, and an image other than that of a coil may be extracted by mistake. Accordingly, in a process of extracting a coil image from the previous mask image A1 and the latest mask image A2, in order to reduce the effects of the movement of the patient's body, subtraction may be performed after positional alignment is conducted by automatic pixel-shifting. When a to-be-treated aneurysm has been specified from a 3D image, only an image of an area around the aneurysm may be extracted from the coil image D1.

Figure 3:
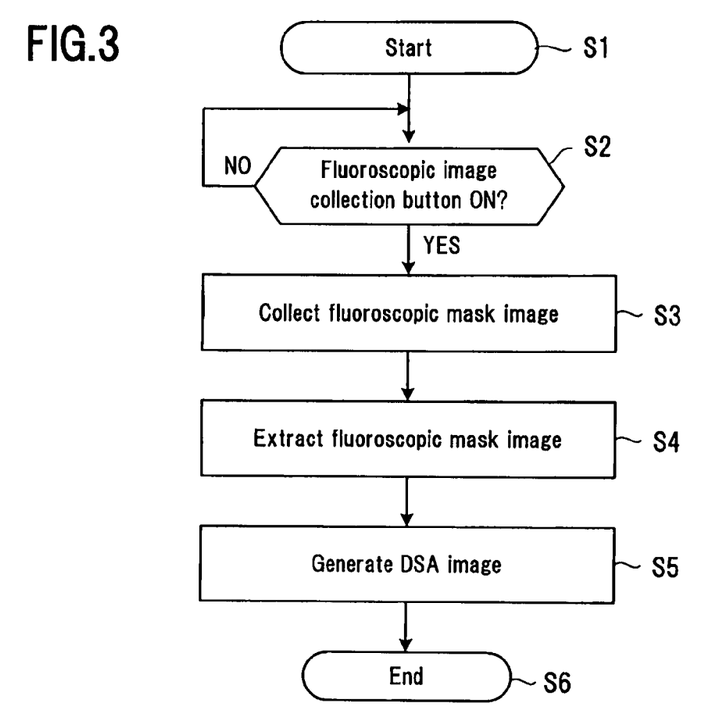
FIG. 3 is a flowchart showing a process of generating a coil image according to an embodiment of the present invention.

FIG. 3 is a flowchart showing a process of generating the coil image D1. Step S1 is a start step. At step S2, a determination is made as to whether a fluoroscopic image collection button has been pushed. The fluoroscopic image collection button is provided in the input unit 33. After the button is pushed by a doctor's operation, a fluoroscopic mask image is collected at step S3. If coils are placed and kept in several stages, the fluoroscopic image collection button is pushed each time a coil is placed and kept, and a plurality of fluoroscopic mask images are collected in chronological order.

Step S4 is a step of extracting a fluoroscopic mask image. From a plurality of fluoroscopic mask images collected in chronological order, fluoroscopic mask images (A1 and A2, for example) that have been collected within a certain period of time are extracted. Subtraction is carried out at the next step S5 to generate a DSA (Digital Subtraction Angiography) image (coil image D1). At step S6, the generation of the coil image D1 comes to an end.

Figure 4:
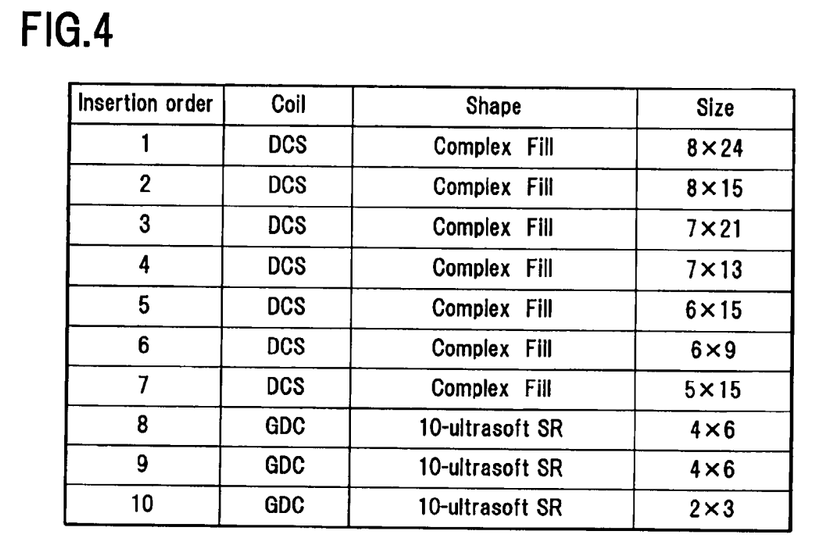
FIG. 4 is an explanatory diagram explaining the order of coils that are placed and kept according to the embodiment.

FIG. 4 is an explanatory diagram showing coils to be inserted. Coils of different sizes and shapes are sequentially placed and kept. For example, suppose that 10 coils are to be inserted. In this case, the subtraction of fluoroscopic mask images A1 and A2 (or A2 and A3, A3 and A4, . . . ) makes it possible to obtain the coil image D1. The coil image D1 is an image of a coil that has already been placed and kept. Therefore, by synthesizing the above image with the guide wire emphasis image E1, it is possible to display the coil that has already been placed and kept and a new coil that will be placed and kept in such a way that the coils can be distinguished from one another.

Incidentally, the fluoroscopic mask images A1 and A2 are different images in terms of time. However, the fluoroscopic mask images A1 and A2 are not limited to the images taken on the same day. The fluoroscopic mask image A1 may be taken at a different time on a different date, for example one or two days or one week before the fluoroscopic mask image A2. Moreover, the real-time fluoroscopic image B1 may be taken at a different time on a different date from the fluoroscopic mask image A2.

In that manner, according to the first embodiment, a new coil can be precisely placed and kept with the positional relation with the already-placed-and-kept coil being taken into consideration. It is also possible to lead a catheter or guide wire to an affected part by watching a roadmap displayed on a 3D vascular display image and to support diagnosis.

(Second Embodiment)

Figure 5:
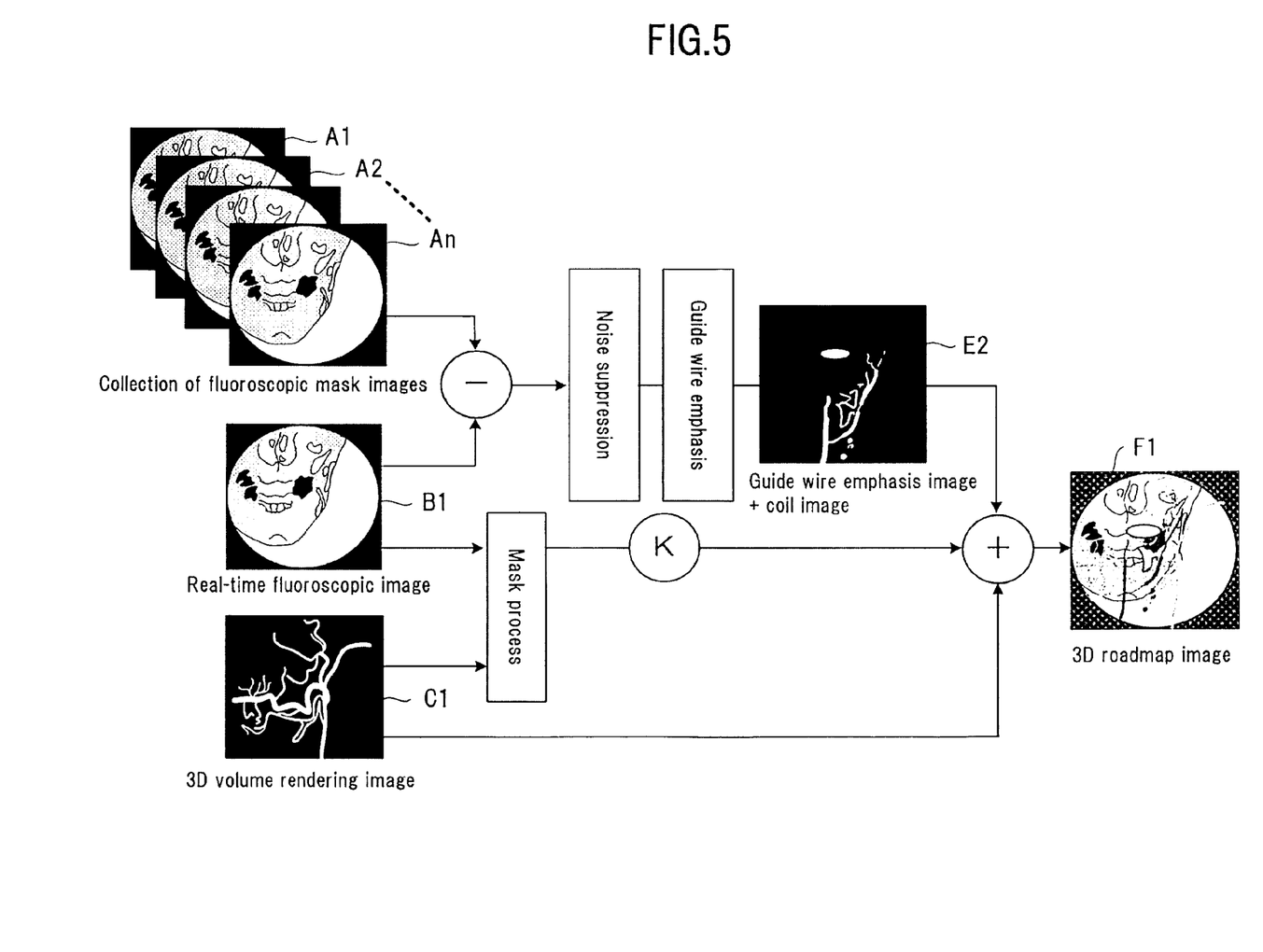
FIG. 5 is an explanatory diagram showing a process of generating a roadmap image according to a second embodiment of the present invention.

The following describes a medical image diagnosis device according to a second embodiment. FIG. 5 is a diagram for explaining an operation, showing a process of generating a 3D roadmap image to be displayed on the display 46 according to the second embodiment.

First, coils are placed and kept. Then, fluoroscopic mask images are each re-created, a plurality of fluoroscopic mask images A1, A2, . . . , An are collected in chronological order and stored and managed in the two-dimensional image memory 34 (mask image storage unit). Then, by performing a subtraction of a fluoroscopic mask image, which is selected from among the previous fluoroscopic mask images A1 to An, and a real-time fluoroscopic image B1, an image E2 of a guide wire and coil is obtained.

The real-time fluoroscopic image B1 is an image depicting the situation where the devices (catheter and guide wire) have been inserted. Therefore, by performing subtraction between the real-time fluoroscopic image B1 and the latest fluoroscopic mask image An, it is possible to obtain an image containing a coil and device that will be placed and kept. By performing noise suppression and wire emphasis processes on the subtraction image, it is possible to obtain a guide wire emphasis image and the coil image E2.

Moreover, by performing a mask process on the real-time fluoroscopic image B1 and a 3D volume rendering image C1, synthesizing the images at a predetermined ratio k, and synthesizing the guide wire emphasis image and the coil image E2, it is possible to obtain a 3D roadmap image F1. In the composite image F1, it is possible to figure out the motion of the guide wire or the like, and display a coil that has already been placed and kept and a coil that is being placed and kept in such a way that the coils can be distinguished from one another, resulting in an increase in visibility.

The fluoroscopic mask images A1 to An are generated by the mask image generation unit 43, and the 3D volume rendering image C1 is generated by the three-dimensional vascular display image generation unit 41. The subtraction of the selected fluoroscopic mask image (one of A to An) and the real-time fluoroscopic image B1 is performed by the difference image generation unit 42. The process of synthesizing each image is carried out by the image synthesis unit 40. According to the second embodiment, the coil image generation unit 44 shown in FIG. 2 can be omitted.

Figure 6:
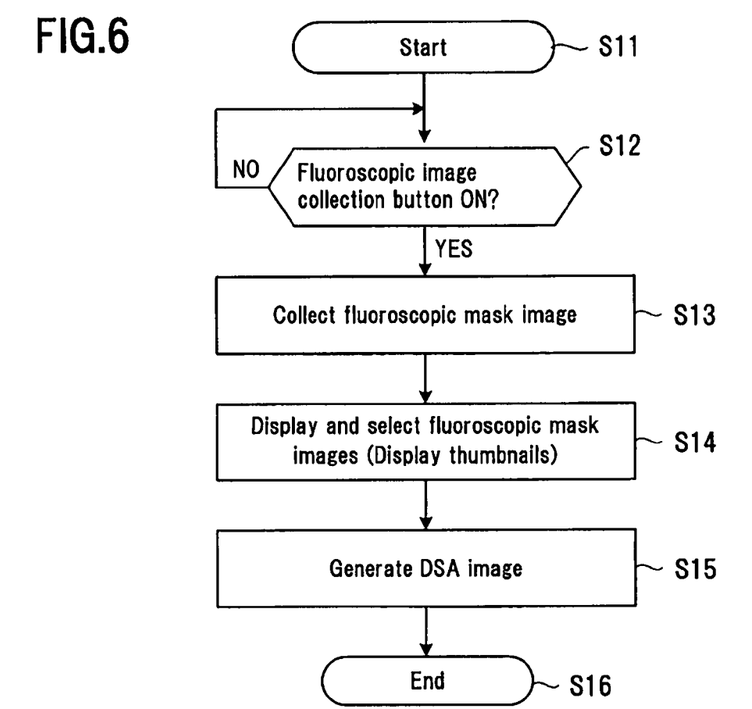
FIG. 6 is a flowchart showing a process of generating a device image according to the second embodiment.

FIG. 6 is a flowchart showing a process of generating the guide wire emphasis image and the coil image E2. Step S11 is a start step. At step S12, a determination is made as to whether a fluoroscopic image collection button has been pushed. The fluoroscopic image collection button is provided in the input unit 33. After the button is pushed by a doctor's operation, a fluoroscopic mask image is collected at step S13.

If coils are placed and kept in several stages, the fluoroscopic image collection button is pushed each time a coil is placed and kept, and a plurality of fluoroscopic mask images A1 to An are collected in chronological order. Step S14 is a step of displaying fluoroscopic mask images for selection. From among a plurality of fluoroscopic mask images A1 to An collected in chronological order, an arbitrary fluoroscopic mask image is selected.

Figure 7:
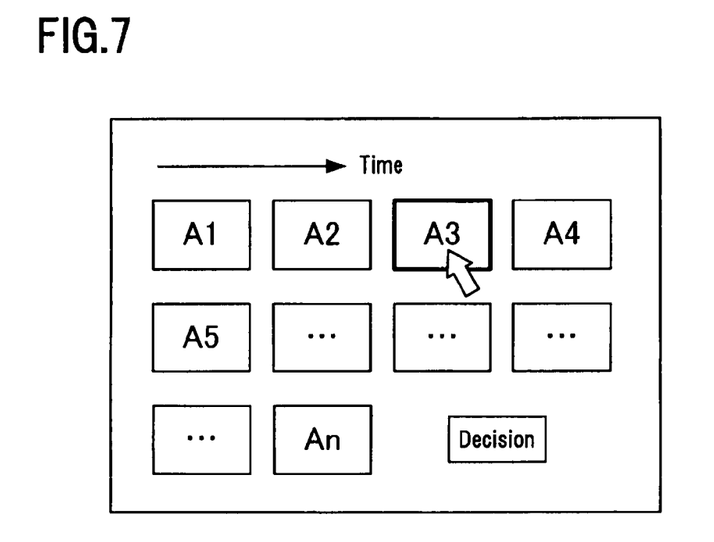
FIG. 7 is an explanatory diagram showing an example of how to select a fluoroscopic mask image according to the second embodiment.

For example, as shown in FIG. 7, a plurality of fluoroscopic mask images A1 to An collected in chronological order are turned into thumbnails. The thumbnail images are displayed and arranged on the display 47 in the order the images are collected (on a time axis). Then, a mouse in the input unit 33 is operated to select one of the images, and the selected image is decided with a decision button. In this manner, the input unit 33 also includes a function of a selection means.

At the next step S15, the subtraction of the fluoroscopic mask image selected and the real-time fluoroscopic image is performed to generate DSA images (a guide wire emphasis image and a coil image E2), and the process comes to an end at step S16. The guide wire emphasis image and the coil image E2 contain an image of a coil that has already been placed and kept. Therefore, it is possible to display the coil that has already been placed and kept and a new coil that will be placed and kept in such a way that the coils can be distinguished from one another.

In that manner, according to the second embodiment, an arbitrary image is selected from a plurality of fluoroscopic mask images, and the subtraction of the selected image and a real-time fluoroscopic image is carried out. As a result, it is possible to confirm the state of a coil at an arbitrary timing among coils that have already been placed and kept. It is also possible to display a new coil that will be placed and kept in such a way that the coil can be distinguished. It is also possible to lead a catheter or guide wire to an affected part by watching a roadmap displayed on a 3D vascular display image and to support diagnosis.

The subtraction of a plurality of fluoroscopic mask images, which are arbitrarily selected from the fluoroscopic mask images A1 to An, and the real-time fluoroscopic image B1 may be sequentially performed to obtain images of a plurality of coils that have been previously placed and kept, the obtained images may be simultaneously displayed in chronological order.

For example, the subtraction of the fluoroscopic mask image A1 and the real-time fluoroscopic image B1 is performed to obtain an image of the first coil placed and kept. Then, the subtraction of a fluoroscopic mask image, which is different in time from the fluoroscopic mask image A1, and the real-time fluoroscopic image B1 is performed to obtain an image of the next coil placed and kept. By synthesizing a plurality of coil images that are sequentially obtained as described above, it is possible to display in chronological order. The coil images may be each displayed in different colors.

According to the above-described embodiments, in an intravascular treatment, a doctor and any other device operator can provide medical care in an efficient manner by visually checking a guide wire, catheter, coil or the like.

While certain embodiments of the inventions have been described, these embodiments have been presented by way of example only, and are not intended to limit the scope of the inventions. Indeed, the novel devices and methods described herein may be embodied in a variety of the other forms; furthermore, various omissions, substitutions and changes in the form of the apparatus and methods described herein may be made without departing from the sprit of the inventions. The accompanying claims and their equivalents are intended to cover such forms or modifications as would fall within the scope and spirit of the inventions.

Reference Signs List

100: Medical image diagnosis device (X-ray image diagnosis device)
10: X-ray generation unit
20: X-ray detection unit
25: Imaging unit
30: Image processing device
31: A/D converter
32: Control unit
33: Input unit
34: Two-dimensional image memory
35: Three-dimensional image memory
36: Filtering unit
37: Affine transformation unit
38: LUT (Look-up table)
39: Reconstruction unit
40: Image synthesis unit
41: Three-dimensional vascular display image generation unit 42: Difference image generation unit
43: Mask image generation unit
44: Coil image generation unit
45: Three-dimensional image acquisition unit
46: D/A converter
47: Display
48: Bus

The invention claimed is:

1. A medical image diagnosis device, comprising:
an imaging unit that includes an X-ray generation unit and an X-ray detection unit;
a mask image generation unit that generates a plurality of mask images that are different in terms of time by processing an image taken by the imaging unit;
a first image generation unit that calculates differences between a latest mask image and another mask image among a plurality of the mask images, and extracts an image of a preceding device that is placed and kept in a blood vessel;
a second image generation unit that calculates differences between the latest mask image and a real-time fluoroscopic image depicting a situation where an insertion device is being inserted into a blood vessel, and generates an image of the insertion device, and then performs emphasis processes on the image of the insertion device;
an image synthesis unit that synthesizes the image of the preceding device generated by the first image generation unit and the image of the insertion device emphasized by the emphasis processes; and
a display that displays an image generated by the image synthesis unit.

2. The device according to claim 1, wherein
the image synthesis unit further synthesizes a three-dimensional vascular display image with the images generated by the first and second image generation units.

3. The device according to claim 1, wherein
the image synthesis unit displays an image of the preceding device and an image of a device other than the preceding device in different color tones.

4. A medical image diagnosis device, comprising:
an imaging unit that includes an X-ray generation unit and an X-ray detection unit;
a mask image storage unit that stores a plurality of mask images that are different in terms of time by processing an image taken by the imaging unit;
a selection unit that selects a mask image to be used from among mask images stored in the mask image storage unit;
an image generation unit that calculates a difference between a mask image selected by the selection unit and a real-time fluoroscopic image depicting a situation where an insertion device is being inserted into a blood vessel, and generates an image of a preceding device that is placed and kept in a blood vessel and an image of an insertion device that has been inserted, and then performs emphasis processes on the image of the insertion device; and
a display that displays an image synthesized from the image of the preceding device and the image of the insertion device emphasized by the emphasis processes.

5. The device according to claim 4, further comprising:
an image synthesis unit that synthesizes the image synthesized from the image of the preceding device and the image of the insertion device emphasized by the emphasis processes with a three-dimensional vascular display image.

6. The device according to claim 4, wherein
the selection unit displays thumbnail images that are arranged in chronological order by processing a plurality of the mask images, and selects the mask image using the thumbnail images.

7. The device according to claim 4, wherein
the image generation unit displays an image of the preceding device and an image of an insertion device other than the preceding device in different color tones.

8. The device according to claim 4, wherein:
the selection unit selects a plurality of arbitrary mask images that are different in terms of time from among the mask images stored in the mask image storage unit;
the image generation unit sequentially performs subtraction of a plurality of the fluoroscopic mask images and the real-time fluoroscopic image to generate a plurality of images of preceding devices; and
a plurality of the images of preceding devices are combined and displayed on the display.

9. A medical diagnosis support method, comprising:
generating a plurality of mask images that are different in image-taking time by processing an image taken by an imaging unit that includes an X-ray generation unit and an X-ray detection unit;
calculating differences between a latest mask image and another mask image among a plurality of the mask images, and extracting an image of a preceding device that is placed and kept in a blood vessel;
calculating differences between the latest mask image and a real-time fluoroscopic image depicting a situation where an insertion device is being inserted into a blood vessel, and generating an image of the insertion device;
performing emphasis processes on the image of the insertion device; and
synthesizing the image of the preceding device and an image of the insertion device emphasized by the emphasis processes, and displaying the synthesized image on a display.

10. A medical diagnosis support method, comprising:
storing in a storage unit a plurality of mask images that are different in terms of time by processing an image taken by an imaging unit that includes an X-ray generation unit and an X-ray detection unit;
selecting a mask image to be used from among mask images stored in the storage unit;
calculating a difference between the selected mask image and a real-time fluoroscopic image depicting a situation where an insertion device is being inserted into a blood vessel, and generating an image of an insertion device that contains a preceding device that is placed and kept in a blood vessel;
performing emphasis processes on the image of the insertion device; and
displaying an image synthesized from the image of the preceding device and the image of the insertion device emphasized by the emphasis processes.

* * * * *